United States Patent [19]

Thiele et al.

[11] 4,214,095

[45] Jul. 22, 1980

[54] CHLOROBENZYL PHENOXY ALKOXYLATES

[75] Inventors: Kurt Thiele; Quazi Ahmed, both of Zofingen; Rudolf Adrian, Vordemwald; Ulrich Jahn, Zofingen, all of Switzerland

[73] Assignee: Siegfried Aktiengesellschaft, Zofingen, Switzerland

[21] Appl. No.: 6,542

[22] Filed: Jan. 25, 1979

[51] Int. Cl.² .............................................. C07C 69/76
[52] U.S. Cl. .................................... 560/57; 562/468; 560/58
[58] Field of Search .................. 562/472, 468; 560/62, 560/57, 58

[56] References Cited

U.S. PATENT DOCUMENTS 4,072,754  2/1978  Schacht et al. ...................... 560/62

FOREIGN PATENT DOCUMENTS 2356655  5/1974  Fed. Rep. of Germany ........... 562/472
6607225  11/1966  Netherlands .............................. 562/472

Primary Examiner—Paul J. Killos
Attorney, Agent, or Firm—Werner W. Kleeman

[57] ABSTRACT

Novel compounds of the formula (1)

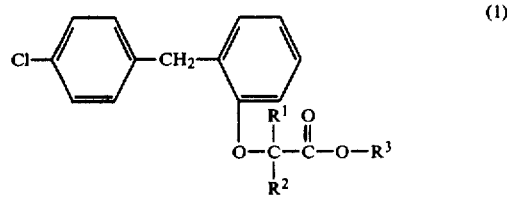

wherein $R^1$ and $R^2$ are different lower alkyls and $R^3$ is a lower alkyl or a methyl pyridine group, and the acid addition salts of formula (1) compounds when $R^3$ is methyl pyridine. The novel compounds have an asymmetric C-atom and may be in the form of the D,L racemates or the D or L stereoisomers.

These compounds are useful in the treatment of hypercholesterolemia and hyperlipidemia because of their high effectiveness in reducing the level of cholesterol and lipids in the blood combined with very low general toxicities and substantially reduced hepatomegalitic effects.

6 Claims, No Drawings

CHLOROBENZYL PHENOXY ALKOXYLATES

BACKGROUND OF THE INVENTION

1. Field of the Invention

The present invention relates to novel diphenyl methane derivatives having improved pharmacological properties when used for the therapy of hypercholesterolemia and hyperlipidemia and more particularly to chlorobenzyl phenoxy alkoxylates wherein the oxyalkoxylic moiety is in ortho position of the phenyl ring and has an asymmetric carbon atom as the link between the phenoxy moiety and the carboxylic function.

2. Description of the Prior Art

Ethyl p-chlorophenoxyisobutyrate (generic name: Clofibrate) having the formula

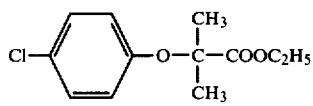

disclosed by Glynn M. Jones et al. in U.S. Pat. No. 3,262,850 is a widely accepted therapeutic agent used for reducing the concentration of cholesterol in the blood serum. The relatively high toxicity ($LD_{50}$ 2350 mg/kg, mice) of Clofibrate and the necessity to use it in relatively high doses because of its low therapeutic effectiveness has triggered the search for other therapeutical agents suitable for treatment of hypercholesterolemia and having improved pharmacological properties.

The above mentioned U.S. Pat. No. 3,262,850 to Jones discloses other compound structures that include the phenoxyisobutyric moiety of the formula (10)

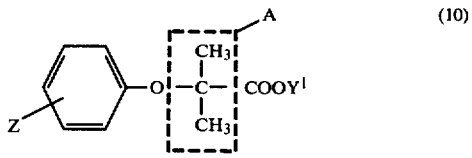

in which Z is at least one substituent in para, meta or ortho position and $Y^1$ is hydrogen or lower alkyl. For reasons explained below, the box A shown in dashed lines indicates the link between phenoxy carboxy.

Fukami et al. in German Published Specification No. 2,356,655 then disclosed anti-hypercholerolemic compounds of the formula

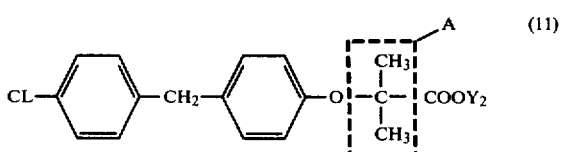

in which $Y^2$ is lower alkyl or a N,N-diloweralkyl substituted aminoalkylene group. It is to be noted that link A of the Fukami compounds (11) is the same as that of the Jones compounds (10).

Applicants have previously disclosed (e.g. in German Published Specification No. 2,461,069) that certain asymmetric homologues of the Jones compounds (10) and the Fukami compounds (11) of the formula (12)

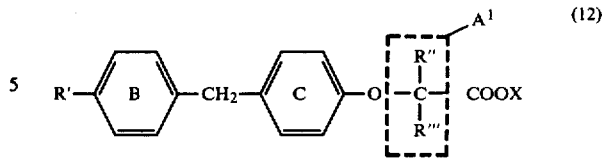

in which R' is hydrogen, halogen, lower alkyl or lower alkoxy and X is lower alkyl, provide for substantial improvements, notably an improved therapeutic ratio ($LD_{50}$ divided by cholesterol lowering effectiveness) if link $A^1$ is asymmetric; preferably, R" and R'" are different lower alkyls having a combined total of at least 3 carbon atoms, e.g. methyl/ethyl, methyl/propyl, etc.

When reviewing other parameters except link $A^1$ of the above formula (12) compounds, both the art referred to above as well as experimental evidence reported below seemed to indicate that the linear arrangement of the formula (12) structure between link $A^1$ and ring B was critical, notably with regard to the paraposition of the methylene and the oxy substituent of Ring C. For example, while some non-linear structures are disclosed in the Jones Patent mentioned above as well as in U.S. Pat. No. 3,362,997 to Bolhofer, and while non-linear structures of the general class of compounds referred to above are disclosed as herbicides in U.S. Pat. No. 4,088,474 to Matterstock et al., linear structures predominate and have been preferred for cholesterol-lowering agents according to the pertinent art.

On the other hand, experimental evidence indicates that relatively low toxicity data (i.e. high $LD_{50}$ values) of compounds of the above classes found to have satisfactory cholesterol lowering effectiveness (i.e. low $ED_{25}$ values) may not be a sufficient criterion in the evaluation of an optimum balance of properties. One generally accepted criterion in the context of drug-testing is the effect of the drug on size and weight of the liver, notably the hepatomegalitic or liver weight increasing effect. This factor is typically measured in terms of the increase of the weight of the hepata (liver) of test animals (e.g. rats) after a period of drug administration. It has been observed that compounds believed to be suitable for treatment of hypercholesterolemia or hyperlipidemia may have an undesirable high hepatomegalitic effect, i.e. cause a significant or even substantial increase of the liver weight of the test animals after a period of drug administration even though the $LD_{50}$ toxicity of such compounds may be acceptably low.

SUMMARY OF THE INVENTION

Accordingly, it is a main object of this invention to provide for novel compounds having an improved balance of pharmacological properties.

Another object of this invention is to provide for novel compounds having low toxicity combined with a satisfactory effectiveness in reducing the concentration of cholesterol in the blood and no or very low effect upon the liver weight.

Another object of the invention is to provide for novel chlorobenzyl phenoxy alkoxylates in which the oxy-alkoxy moiety is in ortho position of the phenyl ring and wherein the alkoxylate moiety is asymmetric.

Further objects will become apparent as the specification proceeds.

According to the present invention we have found a group of novel compounds of the formula (1)

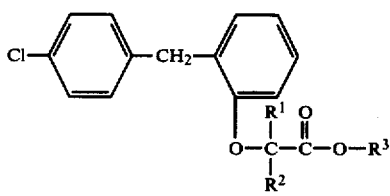

(1)

wherein $R^1$ and $R^2$ are different alkyls of from 1 to 4 carbon atoms each; according to a first preferred embodiment, one of $R^1$ and $R^2$ is methyl while the other is ethyl, propyl or butyl; the combination of methyl/ethyl for $R^1$, $R^2$ is particularly preferred. Due to the provision that $R^1$, $R^2$ are different in the inventive compounds of formula (1), the carbon atoms between $R^1$, $R^2$ is asymmetric or optically active. Accordingly, the invention includes the D-isomers, the L-isomers and the D,L-racemates of the formula (1) compounds.

Preferably, $R^3$ is alkyl of from 1 to 4 carbon atoms, ethyl being a particularly preferred example; $R^3$ could also represent an ion selected from sodium, potassium, calcium, magnesium and aluminum ions; further, $R^3$ can stand for methyl pyridine, i.e. a group of the formula

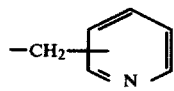

As the annular nitrogen of methyl pyridine is basic, compounds of formula (1), wherein $R^3$ is methyl pyridine, may form salts of addition with acids. For pharmacological use such salts of addition will be those with pharmacologically acceptable acids including mineral or inorganic acids such as hydrochloric, nitric, sulphuric and phosphoric acid and the like, as well as organic acids such as lactic, citric, malic and tartaric acid and the like. Many other pharmacologically acceptable acids are known in the art and can be used for acid addition salts of formula (1) compounds wherein $R^3$ is methyl pyridine. 3-Methyl pyridine (also called nicotinyl) is a preferred specific example of such as $R^3$; for many purposes $C_1$-$C_4$ alkyls are preferred for $R^3$, however.

PREFERRED EMBODIMENTS OF THE INVENTION

The compound of the formula (2)

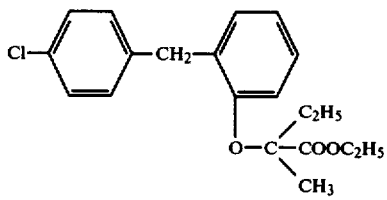

is a particularly preferred example of a compound according to the invention. A specific method of preparing this particular compound will be explained below in the examples but other methods could be used to produce the compound of formula (2) as well as other compounds (1) according to the invention.

According to a first general method, the formula (1) compounds can be obtained by condensing a phenol of the formula (3)

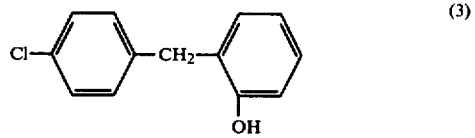

(3)

or the corresponding phenolate such as an alkali metal phenolate, e.g. the sodium or potassium phenolate, with a compound of the formula (4)

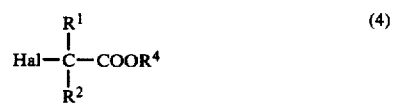

(4)

wherein Hal is a halogen atom such as chlorine, bromine, etc.; $R^1$ and $R^2$ are defined as above and $R^4$ is $R^3$ as defined above or hydrogen or a group that can be converted into $R^3$, e.g. by transesterification. Depending upon the significance of $R^4$ the product of condensing compounds (3) and (4) is the target compound (1) or will have to be converted into a formula (1) compound, e.g. by esterification with the corresponding alcohol $R^3OH$, when $R^4$ is hydrogen, or transesterification.

The use of a base suitable as an acid-binding agent in the condensation of compounds (3) and (4) may be advantageous but is not believed to be critical. Preferably, condensation of (3) and (4) is effected in an organic solvent such as xylene, generally under substantially anhydrous conditions and at elevated temperatures, e.g. up to reflux temperatures of the solvent.

The condensation product can be recovered from the reaction mixture by evaporating the solvent and destillation and/or recrystallization of the residue. The condensation product is generally obtained in the form of the D,L-racemate. The D- and L-stereoisomers could be obtained from the racemate, e.g. by chromatography, but such separation is not believed to be critical.

Specific examples of methods suitable for producing the novel compounds will be given below. These examples are illustrative and not to be understood as limiting the scope of the invention in any way. In the examples, percentages are by weight, temperatures are in degree centigrade. Elemental analysis data are in percent by weight.

EXAMPLE I

Preparation of ethyl D,L-2-methyl-2-[o-(p'-chlorobenzyl)-phenoxy]butyrate (formula 1, $R^1$=ethyl, $R^2$=methyl, $R^3$=ethyl)

A solution of 4'-chloro-2-hydroxy-diphenyl-methane (218.6 g. 1.0 mol) in 1200 ml of dry xylene was added to freshly prepared sodium ethoxide (68.05 g. 1.0 mol) and the mixture was refluxed for 2 hours. A solution of ethyl D,L-2-bromo-2-methylbutyrate (209.10 g, 1.0 mol) in 50 ml of dry xylene was added carefully in a dropwise manner to the mixture during a period of 15 min. The reaction was continued for 22 hours and then allowed to cool to room temperature (20°-25° C.). The reaction mixture was washed twice with 300 ml of 1 N NaOH solution. The organic phase was washed free of alkali with water, dried (over anhydrous magnesium sulfate), and evaporated under reduced pressure to give 196.30 g of a light yellow oil. The product was dissolved in 100 ml of n-hexane. The solution obtained was filtered through a column of basic alumina (500 g) and the colorless oil was distilled to give 98.05 g of the target product, b.p. 156°–157° C./0.01 mm Hg.

Analysis calculated for $C_2OH_{23}ClO_3$: C 69.25, H 6.68, Cl 10.22. Found: C 69.23, H 6.82, Cl 10.30.

EXAMPLE II

Preparation of ethyl D,L-2-methyl-2-[o-(p'-chlorobenzyl)-phenoxy]-valerate (formula 1, $R^1 = C_3H_7$, $R^2 = CH_3$, $R^3 = C_2H_5$)

A solution of 4'-chloro-2-hydroxy-diphenyl-methane (109.30 g, 0.5 mol) in 600 ml of dry xylene was added to sodium ethoxide (34.0 g, 0.50 mol) and the mixture was refluxed for 2 hours. A solution of ethyl D,L-2-bromo-2-methyl-valerate (111.60 g, 0.50 mol) in 25 ml of dry xylene was added dropwise to the mixture during a period of 5 min. The reaction was continued for 22 hours and was worked-up as in Example I to yield 95.0 g of an oily product. Distillation of the product gave 70.0 g of the target product in th form of a colorless oil, b.p. 166°–168° C./0.01 mm Hg.

Analysis calculated for $C_{21}H_{25}ClO_3$: C 69.89, H 6.98, Cl 9.82. Found: C 70.00, H 6.91, Cl 9.66.

EXAMPLE III

Preparation of D,L-2-methyl-2-[o-(p'-chlorobenzyl)-phenoxy]-butyric acid-(3-oxymethyl-pyridine)-ester hydrochloride (formula 1, $R^1 = C_2H_5$, $R^2 = CH_3$, $R^3 = $

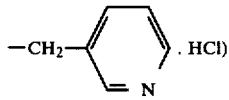

To a solution of D,L-2-methyl-2-[o-(p'-chlorobenzyl)phenoxy]-butyryl-chloride (26.64 g, 0.079 mol) in 50 ml of dry benzene and 7.7 ml of dry pyridine there was added, in a dropwise manner, a solution of 3-hydroxymethyl-pyridine (8.62 g, 0.079 mol) in 10 ml of dry benzene. The mixture was stirred at room temperature for 20 hours. Removal of the solvents under vacuum yielded a brown residue which was treated with 120 ml of 10% $KHCO_3$ solution. The alkaline mixture was extracted with dichloromethane, washed with water and dried over anhydrous magnesium sulfate. The residue obtained after removal of the solvent was dissolved in cyclohexane and filtered through a column of 50.0 g of basic alumina. The light yellow colorless residue was then dissolved in ether and treated with HCl/ether. The hydrochloride was recrystallized twice from acetone to give 15.0 g of the target product in the form of shiny needles, m.p. 114°–115° C.

Analysis calculated for $C_{24}H_{24}ClNO_3HCl$: C 64.58, H 5.65, N 3.14, Cl 15.89. Found: C 64.47, H 5.53, N 3.38, Cl 15.89.

EXAMPLE IV

Preparation of ethyl 2-methyl-2-[o-(p'-chlorobenzyl)-phenoxy]propionate (formula 1, $R^1 = CH_3$, $R^2 = CH_3$, $R^3 = C_2H_5$)

A solution of 4'-chloro-2-hydroxy-diphenyl-methane (109.30 g, 0.50 mol) in 600 ml of dry xylene was added to sodium ethoxide (34.0 g, 0.50 mol) and the mixture was heated under reflux for 2 hours. Thereafter, a solution of ethyl 2-bromoisobutyrate (97.50 g, 0.5 mol) in 25 ml of dry xylene was added dropwise to the mixture during a period of 10 min. After 22 hours, the reaction mixture was worked-up as in Example I to yield an oily product. Destillation yielded 70.0 g of the target product in the form of a colorless oil, b.p. 156° C./0.01 mm Hg.

Analysis calculated for $C_{19}H_{21}ClO_3$: C 68.56, H 6.36, Cl 10.65. Found: C 68.26, H 6.45, Cl 10.45.

EXAMPLE V

Preparation of 2-methyl-2-[o-(p'-chlorobenzyl)-phenoxy]-propionic acid-(3-oxymethyl-pyridine)-ester hydrochloride (formula 1, $R^1 = CH_3$, $R^2 = CH_3$, $R^3 = $

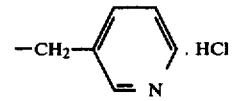

A solution of 3-hydroxymethyl-pyridine (8.07 g, 0.074 mol) in 10 ml of dry benzene was added to a solution of 2-methyl-2-[o-(p'-chlorobenzyl)-phenoxy]-propionyl chloride (23.96 g, 0.074 mol) in 50 ml of dry benzene and 7 ml of dry pyridine. The mixture was stirred at room temperature for 20 hours. Work-up was as in Example I to yield a crystalline residue that was recrystallized from acetone to yield 12 g of the target product in the form of shiny needles, m.p. 119°–121° C.

Analysis calculated for $C_{23}H_{22}ClNO_3HCl$: C 63.90, H 5.36, N 3.24, Cl 16.41. Found: C 63.82, H 5.30, N 3.64, Cl 16.47.

EXAMPLES VI to VIII

The following compounds were prepared according to the method of Example I:

VI: The compound of the formula (6)

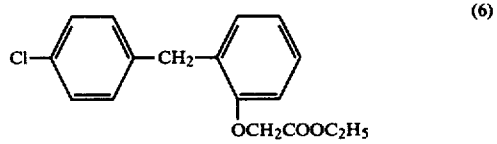

(6)

VII: The compound of the formula (7)

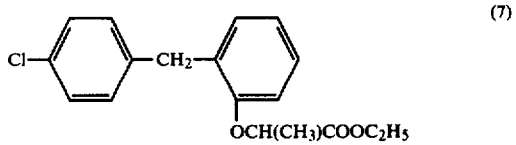

(7)

VIII: The compound of the formula (8)

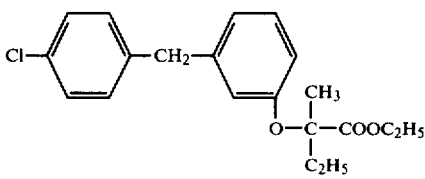

(8)

Pharmacological Data

The compounds of Examples I to VIII were tested to evaluate their pharmacological effectiveness. Specifically, their toxicity ($LD_{50}$), cholesterol-lowering effectiveness ($E_1D_{25}$) and their liver weight increasing activity ($E_2D_{25}$) were tested on animals according to standard methods. The methods are reviewed below and the results are reported in Table I below.

(A) Acute toxicity as $LD_{50}$ lethal dose is given in milligrams of the tested substance per kilogram of body weight (mg/kg) of the test animals; the data reported were determined by the conventional method according to Litchfield and Wilcoxon (J. Pharmacol. 95/1949/p. 99 ff) on mice; the test substance was administered orally once and the mice were observed for a period of 7 days following oral administration or longer if required. At least three different doses were tested for each $LD_{50}$ value given and 10 animals were used for testing of each dose; five test animals were kept in one standard "Macrolon" cage. The test substance was administered as a suspension in aqueous (3-5% by weight) Gum Arabic via a probe into the stomach in quantities of 10 ml of the suspension per kilogram body weight. As is conventional, $LD_{50}$ is that dose of the test substance in mg/kg body weight which causes death of 50% of the test animals within the observation period. Higher $LD_{50}$ values indicate lower toxicity and vice versa.

(B) The effective dose $E_1D_{25}$ is the amount of test substance in milligram per kilogram body weight of the test animals (male Whistar rats, 100-200 g body weight, eight to ten animals per dosis) that causes a 25% by weight reduction of the average cholesterol level in the blood serum of test animals that had received the test substance, compared with the cholesterol level in the blood serum of the control group. The test substances were administered orally via a probe in the manner set forth above for the $LD_{50}$ toxicity, i.e. as suspension in aqueous Gum Arabic. Each test animal was administered daily with 10 ml of the suspension per kilogram body weight. The animals of the control group were administered daily with each 10 ml of the aqueous Gum Arabic per kilogram of body weight without the test substance. The daily dose was administered for 5 subsequent days, resumed after a two-day week-end interval and continued for 5 additional days. After a total test period of two weeks, both the test and the control animals were sacrificed and the blood serum was recovered from the bodies for analysis.

Cholesterol analysis of the serum recovered was carried out according to the standard method of M. Richterich (cf. Monography by M. Richterich, "Klinische Chemie," Verlag Karger, Basel/New York, 1965, p. 232) and the results were evaluated by means of a cholesterol level/dose diagram. The $E_1D_{25}$ values were taken from the diagram thus obtained. Lower $E_1D_{25}$ values indicate higher activity, and vice versa.

(C) The effective dose $E_2D_{25}$ is the amount of test substance in milligram per kilogram body weight of the test animals (male Whistar rats, 100-200 g body weight, eight to ten animals per dose) that causes a 25% increase of the liver weight/body weight ratio (relative liver weight) of test animals that had received that test substance, compared with the liver weight/body weight ratio of the control group. Administration was effected substantially in the manner described above for $E_1D_{25}$. The relative liver weight was determined from the bodies of the sacrificed animals and the control animals. The actual increase of the relative liver weight was evaluated graphically and the $E_2D_{25}$ was obtained by interpolation from the graph.

TABLE I

| Compound | $LD_{50}$ | $E_1D_{25}$ | $E_2D_{25}$ |
|---|---|---|---|
| Example I | >>10,000 | ca. 10 | >300 |
| Example II | >>10,000 | ca. 40 | >100 |
| Example III | >>3000 | ca. 10 | >100 |
| Example IV | >>10,000 | ca. 90 | >100 |
| Example V | >3000 | not measured | >100 |
| Example VI | 3000 | 300 | >300 |
| Example VII | >3000 | 100 | >100 |
| Example VIII | not measured | 40 | 16 |
| Substance A[1] | 8000 | 12.1 | 8.8 |
| Substance B[2] | 2350 | 151 | 136 |

[1] Substance A is the ethyl ester of 2-methyl-2-4'-(4'-chlorobenzyl)-phenoxy-butyric acid prepared according to Example 11 of German Published Patent Application 2,461,069;

[2] Substance B is the ethyl ester of p-chlorophenoxyisobutyric acid (Clofibrate) disclosed in U.S. Pat. No. 3,262,850.

From the results reported in Table I it is apparent that the compounds of Examples I, II and III are preferred, the compound of Example I being particularly preferred because of low toxicity combined with high cholesterol lowering effectiveness and low or very low liver enlargement activities.

The compounds of Examples IV and V are less preferred.

On the other hand, the compounds of Examples VI and VII have a reduced cholesterol lowering effect and the compound of Example VIII is not encompassed by the invention.

Substances A and B are prior art compounds shown for comparative purposes only.

Inventive compounds of the above formula (1) are suitable for therapeutic purposes and can be used in a manner analoguous to that disclosed in U.S. Pat. No. 3,262,850 incorporated herein by reference for purposes of disclosure.

Various modifications of the above disclosed specific embodiments of the invention will be readily apparent to those skilled in the art. It is the applicant's intention to cover by their claims all those changes and modifications which could be made to the embodiments of the invention herein chosen for purposes of the disclosure without departing from the spirit and scope of the invention.

Protection by Letters Patent of this invention in all its aspects as the same are set forth in the appended claims is sought to the broadest extent that the prior art allows.

What is claimed is:

1. A compound of the formula (1)

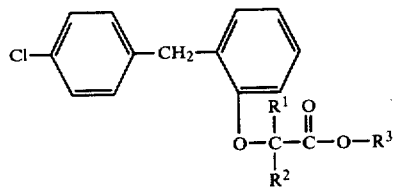
(1)

wherein $R^1$ and $R^2$ are different alkyls of from 1 to 4 carbon atoms and $R^3$ is selected from the group consisting of alkyls having from 1 to 4 carbon atoms and methyl pyridine; and the acid addition salts of said formula (1) compound with a pharmaceutically acceptable acid when $R^3$ is methyl pyridine.

2. The compound of claim 1 wherein $R^3$ is an alkyl selected from the group consisting of propyl and butyl.

3. The compound of claim 2 wherein $R^2$ is selected from the group consisting of ethyl and propyl.

4. The compound of claim 2 wherein $R^3$ is ethyl.

5. The compound of formula (2)

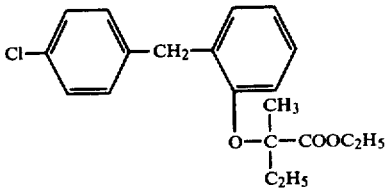
(2)

in the form of the D,L-racemate and the D- and L-stereoisomers of the formula (2) compound.

6. A compound of the formula

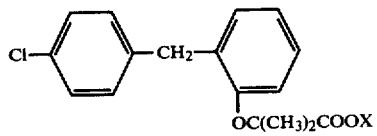

wherein X is selected from the group consisting of alkyls having from 1 to 4 carbon atoms and methyl pyridine; and the acid addition salts of said compound with a pharmaceutically acceptable acid when X is methyl pyridine.

* * * * *